US00PP11376P

United States Patent [19]

Heims

[11] Patent Number: Plant 11,376

[45] Date of Patent: May 9, 2000

[54] HEUCHERA PLANT NAMED 'FIREWORKS'

[75] Inventor: Dan M. Heims, Portland, Oreg.

[73] Assignee: Terra Nova Nurseries, Inc., Tigard, Oreg.

[21] Appl. No.: 09/073,005

[22] Filed: May 5, 1998

[51] Int. Cl.[7] ..... A01H 5/00

[52] U.S. Cl. ..... Plt./263

[58] Field of Search ..... Plt./263

[56] References Cited

U.S. PATENT DOCUMENTS

P.P. 10,441 6/1998 Bloom ..... Plt./263

*Primary Examiner*—Howard J. Locker
*Assistant Examiner*—Kent L. Bell
*Attorney, Agent, or Firm*—Klarquist Sparkman Campbell Leigh & Whinston, LLP

[57] ABSTRACT

A new and distinct hybrid of Heuchera plant characterized by unusual coral-colored flowers, produced abundantly over a long bloom period above old-bronze-colored foliage.

1 Drawing Sheet

The present invention relates to a new and distinct hybrid of Heuchera that originated as a hybrid of two Heucheras in the Saxifrage family (Saxifragaceae).

The new Heuchera is a result of crossing Heuchera 'Palace Passion' (an unpatented Terra Nova hybrid)(seed parent) and an unnamed coral-color-flowered seedling of *Heuchera sanguinea* (unpatented)(pollen parent) at Terra Nova Nurseries, Inc., in Canby, Oreg. This hybrid was selected from a large selection of seedlings. Seed and pollen parent plants were retained to observe habit and to compare with the new variety. The new variety has been reproduced only by asexual propagation (division and tissue culture). Each of the progeny exhibits characteristics to the original plant and is unlike any Heuchera offered by any American nursery or book, known to me, as evidenced by the following characteristics:

Unusual coral-colored flowers, produced abundantly over a long bloom period.
Old-bronze-colored foliage.

Asexual propagation by division and tissue-culture as done in Tigard, Oreg., shows that the foregoing characteristics and distinctions come true to form and are established and transmitted through succeeding propagations.

BRIEF DESCRIPTION OF THE DRAWING

The drawing shows Heuchera 'Fireworks' in bloom in Canby, Oreg. The drawing depicts the plant as true to type as is photographically possible.

DETAILED PLANT DESCRIPTION

The following is a detailed description of the new Heuchera hybrid based on observations of specimens in Canby, Oreg. The color descriptions are all based on *The Royal Horticultural Society Colour Chart* and the *American Rhododendron Society* publication: "A Contribution Toward Standardization of Color Names in Horticulture."

Foliage:
- *Type.*—Evergreen in Canby, Oreg.
- *Shape.*—Ovate, 7-lobed.
- *Length.*—to 7.5 cm (3 in).
- *Width.*—To 8 cm (3.25 in).
- *Petiole length.*—10–12 cm (4–4.75 in).
- *Margins.*—Undulate-dentate, ciliolate.

- *Apex.*—Acute.
- *Base.*—Cordate.
- *Texture.*—Slightly rugose.
- *Leaf arrangement.*—Basal clump.
- *Venation.*—Reticulate.

Flower:
- *Petal count.*—3–4 bracts, 5 petals.
- *Flower shape.*—Campanulate.
- *Flower type.*—Complete, calyx tube cylindrical, stamens not exserted.
- *Ovary.*—Partly inferior.
- *Carpels.*—2 cells.
- *Stamens.*—5.
- *Flower size.*—To 1 cm.
- *Flower number.*—Average 80–100 per panicle.
- *Blooming habit.*—Hoary panicles to 45 cm high and 7 cm wide.
- *Bloom period.*—8–12 weeks from late May to early July.
- *Fragrance.*—None.
- *Lastingness on the plant.*—From two to three weeks (panicles).

Size:
- *Height.*—21 cm.
- *Spread.*—61 cm. (Measurements are from 3-year-old plants grown in Canby, Oreg.).

Fruit:
- *Type.*—Dehiscent capsule.
- *Fertility.*—Fertile.

Hardiness: Cold hardy to Zone 4 (−34 to −29 ° C.). Herbaceous in Zone 4. Plants will remain evergreen in Zones 5 (−29 to −23° C.) and above.

Disease: Somewhat resistant to mildew. Have not observed many diseases affecting plants grown in Canby, Oreg.

Color characteristics:
- *Foliage.*—Mature leaves upper surface—spring and fall: R.H.S. Greyed Purple Group 187C (Dark Red ARS). Metallic Sheen. Mature leaves upper surface—summer and winter: R.H.S. Yellow Green Group 147A. Lower surface: R.H.S. Greyed Purple Group 184C (Moderate Purplish Red ARS).
- *Flowers.*—Buds: R.H.S. Orange Red Group 31 B (Strong Reddish Orange ARS). Flowers: R.H.S. Red Group 39 B (Deep Yellowish Pink ARS).
- *Peduncle.*—R.H.S. Greyed Purple Group 187C.
- *Fruit.*—R.H.S. Yellow-Green Group 152A.

DESCRIPTION OF PARENT PLANTS

The first parent is Heuchera 'Palace Passion,' a Terra Nova hybrid of *Heuchera americana* and *Heuchera sanguinea*. Heuchera 'Palace Passion' has fleshy bronzed leaves and small pink flowers. The other parent is a *Heuchera sanguinea* with short coral blooms and hirsute green leaves.

I claim:

1. A new and distinct hybrid of Heuchera plant substantially as shown and described, characterized by unusual coral-colored flowers, produced abundantly over a long bloom period above old-bronze colored foliage.

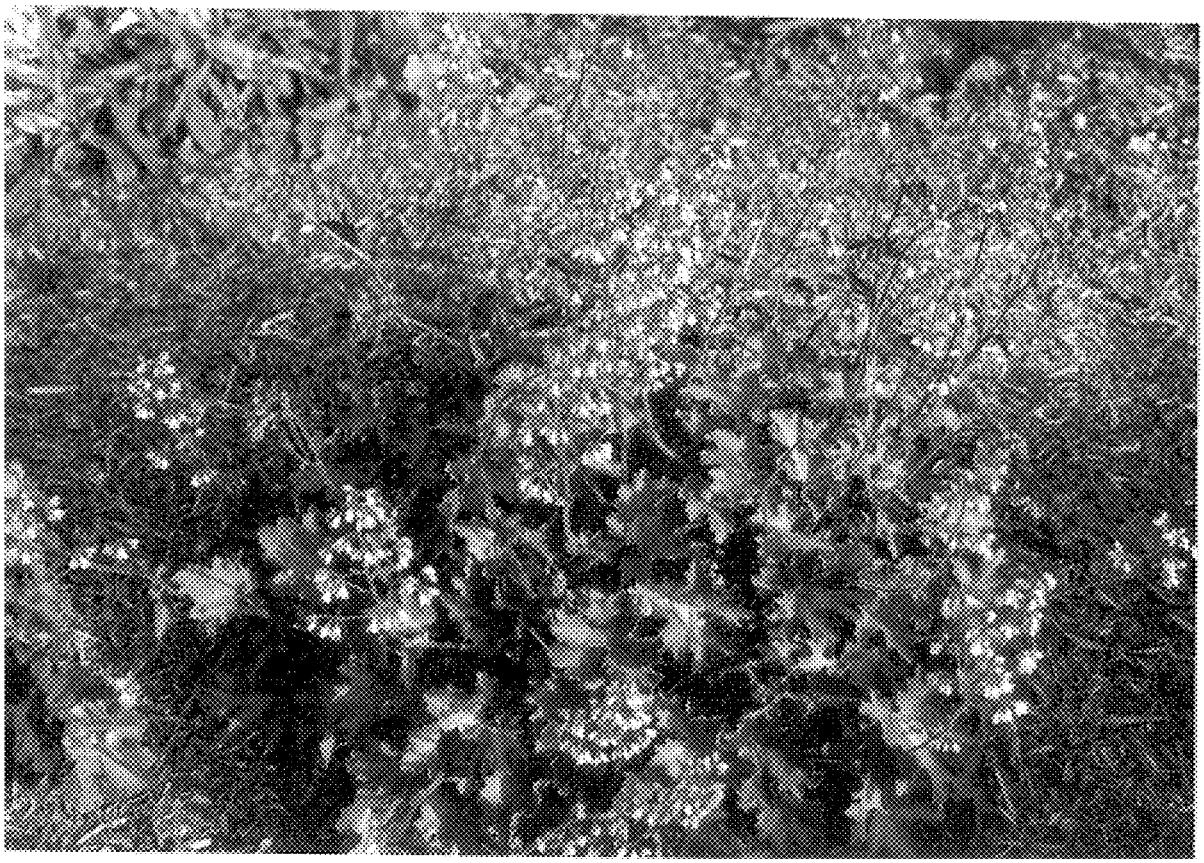

* * * * *